US008469934B2

(12) United States Patent
Weiner et al.

(10) Patent No.: US 8,469,934 B2
(45) Date of Patent: Jun. 25, 2013

(54) PULSATILE PERI-CORNEAL DRUG DELIVERY DEVICE

(75) Inventors: Alan L. Weiner, Arlington, TX (US); Bhagwati P. Kabra, Euless, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 86 days.

(21) Appl. No.: 13/012,885

(22) Filed: Jan. 25, 2011

(65) Prior Publication Data

US 2011/0184358 A1  Jul. 28, 2011

Related U.S. Application Data

(60) Provisional application No. 61/298,577, filed on Jan. 27, 2010.

(51) Int. Cl.
| A61F 9/00 | (2006.01) |
| A61K 9/00 | (2006.01) |
| A61K 31/192 | (2006.01) |
| A61K 31/216 | (2006.01) |
| A61K 31/191 | (2006.01) |
| A61P 27/02 | (2006.01) |

(52) U.S. Cl.
USPC ........... 604/294; 604/289; 604/290; 604/295; 604/296; 604/298; 604/299; 604/300; 604/301; 424/427; 424/428

(58) Field of Classification Search
None
See application file for complete search history.

(56) References Cited

U.S. PATENT DOCUMENTS

| 3,416,530 A | 12/1968 | Ness |
| 3,692,027 A * | 9/1972 | Ellinwood, Jr. ............ 604/891.1 |
| 3,828,777 A | 8/1974 | Ness |
| 3,845,201 A | 10/1974 | Haddad et al. |
| 3,949,750 A | 4/1976 | Freeman |
| 3,961,628 A | 6/1976 | Arnold |
| 4,014,335 A | 3/1977 | Arnold |
| 4,135,514 A | 1/1979 | Zaffaroni et al. |
| 4,164,559 A | 8/1979 | Miyata et al. |
| 4,179,497 A | 12/1979 | Cohen et al. |
| 4,186,184 A | 1/1980 | Zaffaroni |
| 4,343,787 A | 8/1982 | Katz |
| 4,592,752 A | 6/1986 | Neefe |
| 4,730,013 A | 3/1988 | Bondi et al. |
| 5,053,030 A | 10/1991 | Herrick et al. |

(Continued)

FOREIGN PATENT DOCUMENTS

| EP | 0 033 042 | 8/1984 |
| EP | 0 251 680 | 4/1992 |
| WO | 99/37260 | 7/1999 |
| WO | 2007/106557 | 9/2007 |
| WO | 2008/141047 | 11/2008 |
| WO | 2010/101758 | 9/2010 |

OTHER PUBLICATIONS

Cohen excerpt of a dissertation submitted to MIT, "Biocompatability of an Implantable Ophthalmic Drug Delivery Device", 2007.

(Continued)

*Primary Examiner* — Loan Thanh
*Assistant Examiner* — Andrew S Lo
(74) *Attorney, Agent, or Firm* — Scott A. Chapple

(57) ABSTRACT

The present invention is directed to a pulsatile ophthalmic peri-corneal drug delivery device. The device includes an annular body and a mechanism for releasing multiple separate and distinct doses of a therapeutic composition over an extended period of time.

11 Claims, 3 Drawing Sheets

U.S. PATENT DOCUMENTS

| | | | |
|---|---|---|---|
| 5,322,691 | A | 6/1994 | Darougar et al. |
| 5,469,867 | A | 11/1995 | Schmitt |
| 5,725,493 | A | 3/1998 | Avery et al. |
| 5,830,173 | A | 11/1998 | Avery et al. |
| 6,196,993 | B1 | 3/2001 | Cohan et al. |
| 6,251,090 | B1 | 6/2001 | Avery et al. |
| 2002/0099359 | A1 | 7/2002 | Santini, Jr. et al. |
| 2003/0069560 | A1* | 4/2003 | Adamis et al. ............... 604/521 |
| 2006/0177483 | A1* | 8/2006 | Byrne et al. ................. 424/427 |
| 2006/0258994 | A1 | 11/2006 | Avery |
| 2008/0039792 | A1 | 2/2008 | Meng et al. |
| 2008/0181930 | A1 | 7/2008 | Rodstrom et al. |
| 2008/0243095 | A1* | 10/2008 | Kaiser et al. ................. 604/294 |
| 2009/0093780 | A1 | 4/2009 | Tuitupou et al. |
| 2009/0143752 | A1 | 6/2009 | Higuchi et al. |
| 2010/0069857 | A1* | 3/2010 | Christensen ................. 604/300 |
| 2010/0215720 | A1* | 8/2010 | Garagorri Ganchegui et al. ............................ 424/427 |
| 2010/0226962 | A1 | 9/2010 | Rodstrom et al. |

OTHER PUBLICATIONS

Maloney et al., 2005, Electrothermally activated microchips for implantable drug delivery and biosensing, Journal of Controlled Release, 109:244-255.

Urtti et al., 1990, Controlled drug delivery devices for experimental ocular studies with timolol. 1. In vitro release studies, International Journal of Pharmaceutics, 61:235-240.

Urtti et al., 1990, Controlled drug delivery devices for experimental ocular studies with timolol. 2. Ocular and systemic absorption in rabbits, International Journal of Pharmaceutics, 61:241-249.

PCT International Search Report for corresponding PCT/US2011/022310 with mailing date May 11, 2011.

PCT International Written Opinion for corresponding PCT/US2011/022310 with mailing date May 11, 2011.

* cited by examiner

PULSATILE PERI-CORNEAL DRUG DELIVERY DEVICE

CROSS-REFERENCE TO RELATED APPLICATION

This application claims priority under 35 U.S.C. §119 to U.S. Provisional Patent Application No. 61/298,577, filed Jan. 27, 2010, the entire contents of which are incorporated herein by reference.

TECHNICAL FIELD OF THE INVENTION

The present invention relates generally to the field of ocular devices, pharmaceutics, and methods of drug delivery to the eye. More particularly, it concerns pulsatile peri-corneal ocular devices for the sustained pulsatile delivery of a therapeutic compound to the eye.

BACKGROUND OF THE INVENTION

The pharmaceutical industry has developed a variety of techniques for delivering ophthalmic compositions, particularly those that include therapeutic agents, to the eye. Typical ophthalmic drug delivery techniques include topical application of ophthalmic compositions to the eye (e.g., by drops directly onto the eye) and intravitreal injections, which involve delivery of ophthalmic compositions to the vitreous of the eye with a needle (e.g., a syringe). Both of these techniques have drawbacks. One particular drawback common to both of these techniques is the frequency with which an individual must apply the ophthalmic compositions to best treat ophthalmic maladies such as glaucoma, age related macular degeneration (AMD) and others. Patients often forget or otherwise fail to administer drops to their eyes and patients can miss doctor appointments and fail to receive their needed injections.

In view of these drawbacks, the pharmaceutical industry has dedicated significant resources to the development of implantable drug delivery devices that provide sustained delivery of ophthalmic compositions and/or therapeutic agents to the eye. Such devices are typically designed to provide a continuous supply of therapeutic agent to the eye over an extended period of time.

Various ocular drug delivery implants have been described in an effort to improve and prolong drug delivery. For example, U.S. Pat. No. 3,949,750 discloses a punctal plug made of a tissue-tolerable, readily sterilizable material, such as Teflon, HEMA, hydrophilic polymer, methyl methacrylate, silicone, stainless steel or other inert metal material. It is stated that the punctal plug may be impregnated with ophthalmic medication or that the punctal plug may contain a reservoir of the ophthalmic drug.

U.S. Pat. No. 5,053,030 discloses an intracanalicular implant that can be used as a carrier or medium for distributing medications throughout the body. U.S. Pat. No. 5,469,867 discloses a method of blocking a channel, such as the lacrimal canaliculus by injecting a heated flowable polymer into the channel and allowing it to cool and solidify. The polymer may be combined with a biologically active substance that could leach out of the solid occluder once it has formed in the channel.

WO 99/37260 discloses a punctal plug made of a moisture absorbing material, which is not soluble in water, such as a modified HEMA. It is also disclosed that an inflammation inhibitor, such as heparin, may be added to the material from which the punctal plug is made.

U.S. Pat. No. 6,196,993 discloses a punctal plug containing glaucoma medication. The medication is contained in a reservoir within the plug. The reservoir is in fluid communication with a pore through which the medication is released onto the eye.

U.S. Pat. No. 4,592,752 discloses a corneal drug delivery device. The device is substantially the size and curvature of the cornea upon which it is placed and it includes an aperture substantially the size and shape of the pupil of the eye.

More recently, implantable devices have been developed for providing pulsatile or intermittent doses of therapeutic agent to the eye. Examples of such devices are disclosed in U.S. Pat. Nos. 5,725,493; 5,830,173; and 6,251,090 and U.S. Patent Publication No. 2008/0039792, all of which are specifically incorporated herein by reference for all purposes.

U.S. Patent Application No. 2008/0181930 discloses a drug delivery device having a body that includes a matrix of a therapeutic agent and another material such as silicon. The body is coated with a material such as parylene and one or more pores extend from the outer surface of the coating to the outer surface of the body to allow for release of therapeutic agent.

U.S. Provisional Patent Application No. 61/157,010, which is incorporated herein by reference for all purposes, discloses a peri-corneal drug delivery device. A preferred embodiment of the device includes an inner matrix core surrounded by an outer coating. The outer coating includes one or more openings extending to the core for allowing sustained drug release from the inner matrix core.

Each of these devices can provide for some degree of sustained delivery of an ophthalmic composition. However, these devices, as well as other conventional devices, typically suffer from one or more drawbacks. As one example, many conventional devices require that they be applied through an invasive surgical procedure. As another example, many conventional devices have difficulty delivering desired amounts of therapeutic agent for desired amounts of time. As another example, many conventional devices have difficulty delivering therapeutic agent in particular quantities at particular times as may be needed or desired. As yet another example, many devices have difficulty maintaining their desired location relative to the eye and can be lost or undesirably moved. As still another example, many conventional devices can cause discomfort. Thus, there is a need for an ophthalmic drug delivery device that can overcome one, two or more of these drawbacks.

SUMMARY OF THE INVENTION

The present invention is directed to an ophthalmic pulsatile pericorneal drug delivery device. The device includes an annular body sized and shaped to reside upon a conjunctiva of a human eye and extend substantially entirely about a cornea of the human eye when the annular body is disposed upon the human eye. The device further includes a therapeutic composition associated with the annular body. The therapeutic composition is preferably divided into a plurality of separate and distinct units. The device also includes at least one opening for releasing the therapeutic composition wherein the therapeutic composition is released through the at least one opening topically to the eye as multiple separate doses through repeated release of one or more of a plurality of separate and distinct units. In a preferred embodiment, the therapeutic composition in divided into the plurality of separate and distinct units within the device or annular body and/or prior to release from the device.

The device, the annular body or both can include a contact surface that is shaped and sized to correspond to and contact the conjunctiva of the human eye upon application of the device to the eye. That contact surface of the device including all portions that contact the conjunctiva will typically have a surface area that is at least 77 mm² and is typically no greater than 220 mm². Preferably, the device has a volume that is at least at least 14 mm³ and is no greater than 100 mm³.

In one embodiment, the annular body includes a plurality of separate reservoirs, each of the plurality of reservoirs containing one of the separate and distinct unit of the plurality of units, In such an embodiment, the device will also include a plurality of openings separately and respectively associated with the plurality of separate reservoirs for providing fluid communication to the plurality of reservoirs and will includes a plurality of doors for separately and respectively covering the plurality of openings. Preferably each door of the plurality of doors is opened at a separate and distinct point in time to provide for separate release of the separate and distinct units over an extended period of time. In one preferred embodiment, the plurality of doors are formed of an erodible material that is configured to erode is a manner that allows the distinct units to exit the annular body at separate and distinct periods of time.

The present invention is also directed to a method of treating an ophthalmic disease. Accordingly, the device can be disposed upon the eye to intermittently release therapeutic composition topically to the eye.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
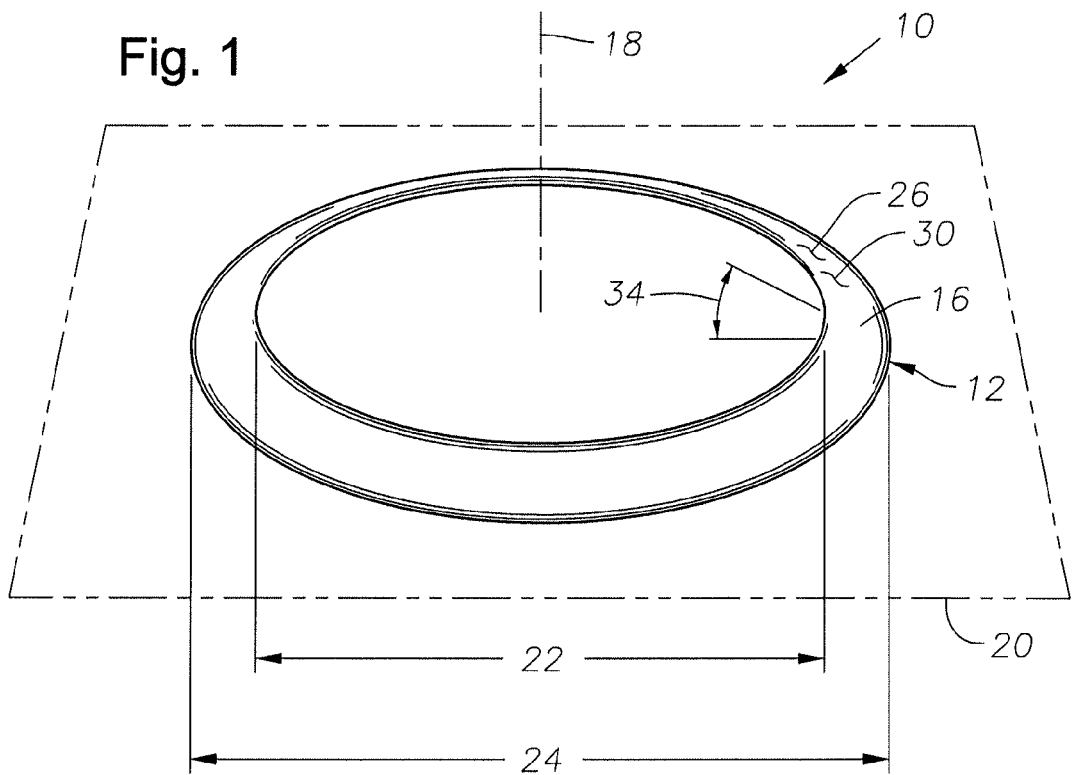
FIG. 1 is a perspective view of an exemplary peri-corneal drug delivery device structure suitable for use with the invention of the present application.

The present invention is predicated upon the provision of a pulsatile peri-corneal drug delivery device. The device is typically annular and is configured to be disposed upon the conjunctiva and/or cornea and, preferably, substantially extends about and/or substantially surrounds the cornea. The device will include a mechanism for assisting the device in providing pulsatile release (i.e., release of separate and distinct units or doses) of therapeutic composition to the eye, particularly the corneal surface of the eye, of a mammal (e.g., a human being) from one or more reservoirs of therapeutic composition. The mechanism will typically allow for pulsatile release from a single reservoir or multiple reservoirs of therapeutic composition.

In one embodiment, the pulsatile drug delivery device includes either a single reservoir of therapeutic composition which contains all of the doses of the therapeutic composition or includes multiple reservoirs of therapeutic composition where each of the multiple reservoirs includes multiple doses of therapeutic composition. In such an embodiment, the mechanism for assisting in providing pulsatile release will typically include one or more openings that provide fluid communication between the reservoir[s] and an environment external the device. The mechanism will also typically include a door that can be selectively opened and closed to allow release of the therapeutic composition from the reservoir[s]. Preferably, the door[s] can be opened and closed to allow for the release of multiple separate single doses of the therapeutic composition over an extended time period.

In an alternative embodiment, the therapeutic composition is divided within the device into multiple separate distinct units wherein each of the units or a subset of the multiple units preferably provides a single dose of therapeutic composition. In such an embodiment, the mechanism for assisting in providing pulsatile release will typically include one or more openings that provide fluid communication between one or more reservoirs and an environment external the device. The multiple separate units can be located within a single reservoir or multiple reservoirs within the device. For example, each unit of the multiple units may be located within its distinct reservoir of multiple reservoirs of the device and be releasable as a single dose. Alternatively, multiple units may be located within a reservoir where each unit is separately releasable from the device to form a single dose. In embodiments where one unit or a subset of the multiple units are disposed in multiple different reservoirs, the mechanism for assisting in providing pulsatile release will typically include one or more openings for each separate reservoir to provide fluid communication thereto and one or more doors for at least temporarily prohibiting and then subsequently allowing fluid communication between the reservoir[s] and an environment external the device. In embodiments where the multiple different units are in a single reservoir, their may only need be a single opening to provide for fluid communication between the reservoir and an environment external the device. Moreover, a door will typically be optional for prohibiting and then subsequently allowing the fluid communication.

It should be understood, that the terms "separate" and "distinct", as they apply to the units and doses of therapeutic composition, have particular meaning for the devices of the present invention. As they apply to units, those terms suggest there is an identifiable physical element that separates the units. That physical element could be a physical space that is between and separates the units. Alternatively, that physical element could be an interface where one of the units abuts the other. It is contemplated that the "separate" and/or "distinct" units may be connected to each other, however, the physical element dividing the units from each other will always exist. Preferably, the units are unconnected relative to each other and may not even contact each other particularly while in the one or more reservoirs of the device. As these terms apply to doses, they mean that one dose will be substantially completely released (i.e., at least 90% and more preferably at least 95% by weight of the therapeutic composition has been released) to the environment external of the device, which will typically be tear fluid or film external of the eye, before a separate and/or distinct dose begins release to the environment external of the device.

Figure 2:
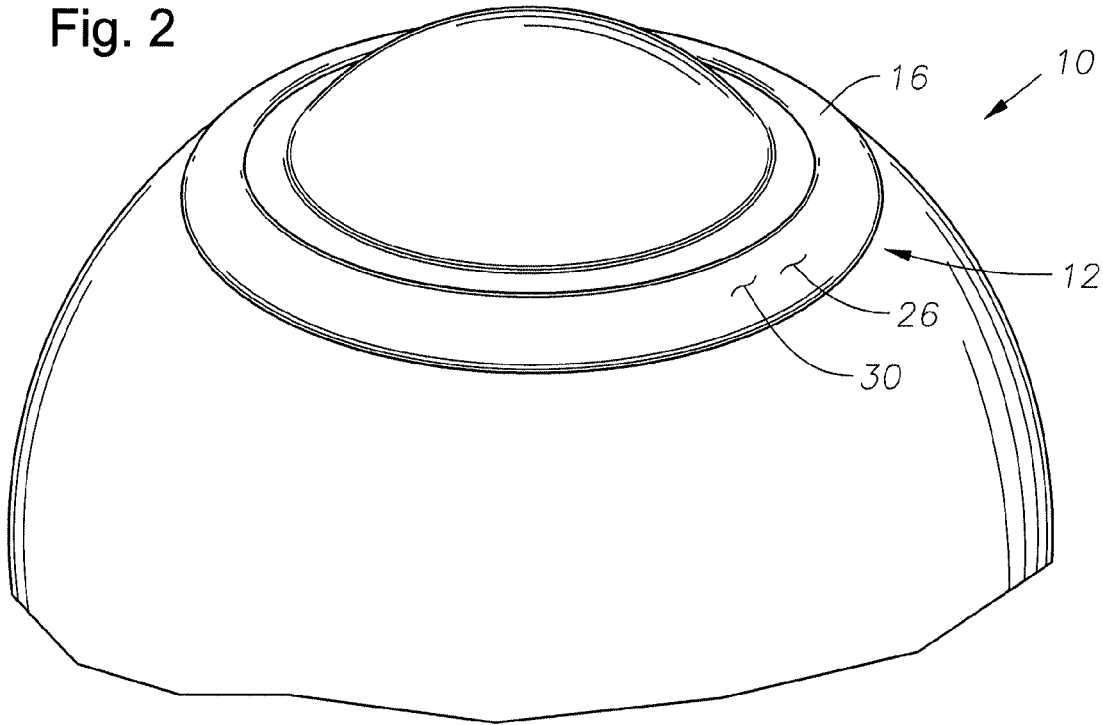
FIG. 2 is a perspective view of the structure of FIG. 1 shown as applied to an eye.
Figure 3:
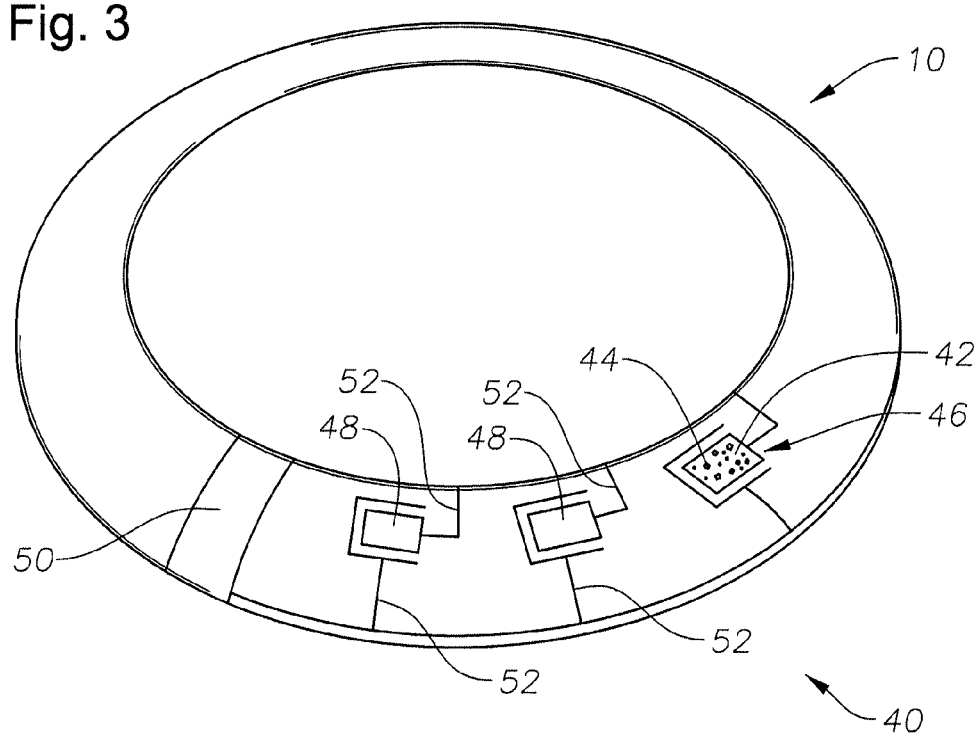
FIG. 3 is a perspective view of one embodiment of a pulsatile peri-corneal drug delivery device in accordance with an aspect of the present invention.
Figure 5:
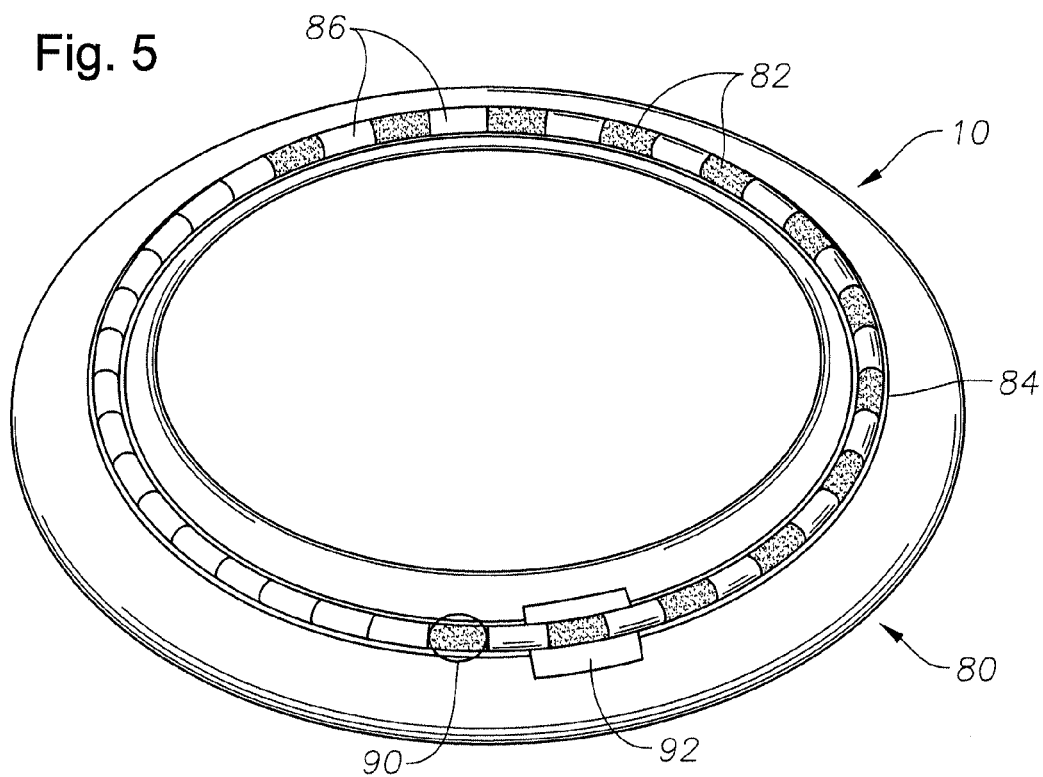
FIG. 5 is a perspective view of yet another embodiment of a pulsatile peri-corneal drug delivery device in accordance with an aspect of the present invention.
Figure 4:
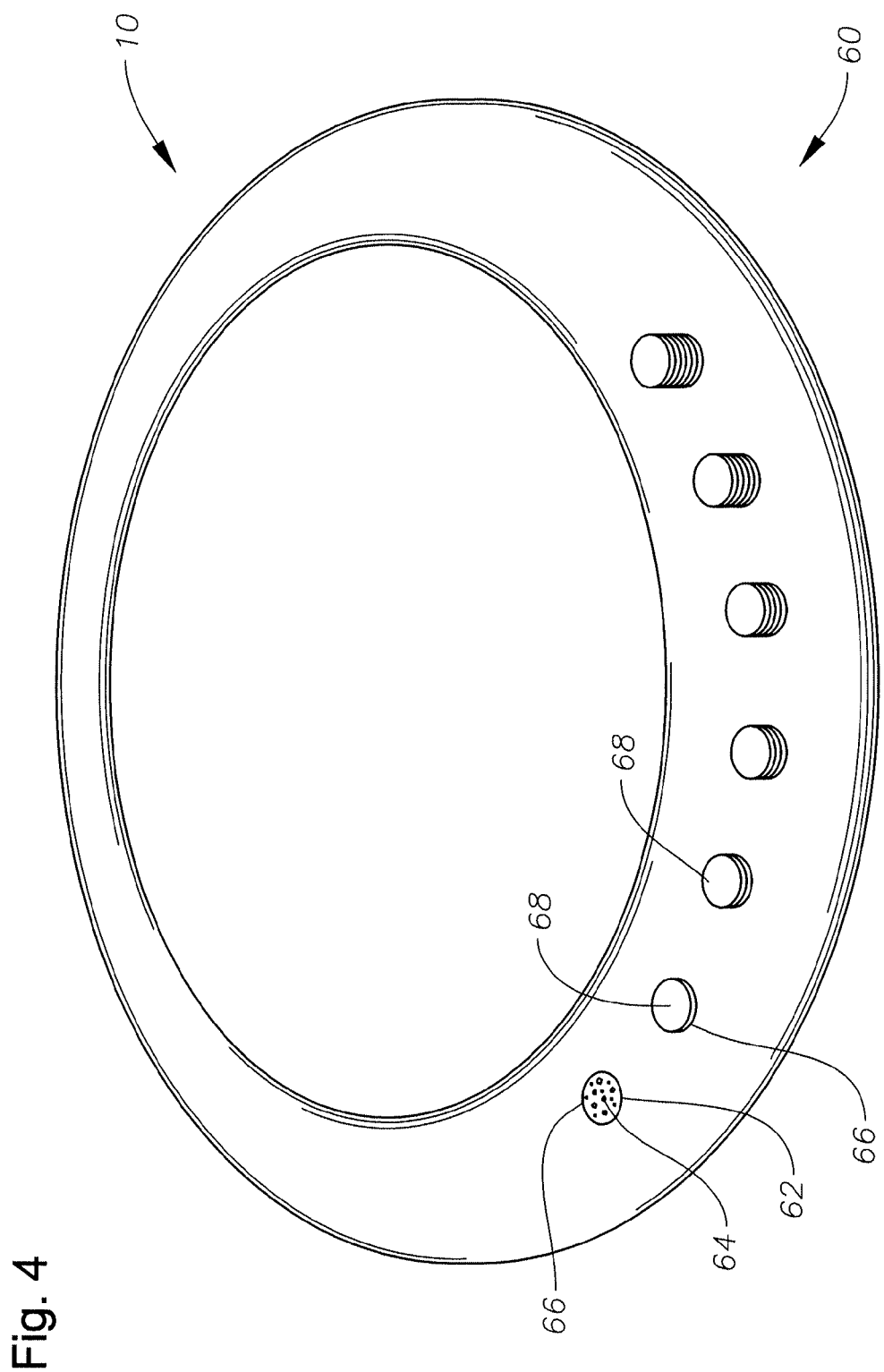
FIG. 4 is a perspective view of another embodiment of a pulsatile peri-corneal drug delivery device in accordance with an aspect of the present invention.

With reference to FIGS. 1 and 2, there is illustrated an annular peri-corneal structure 10 that, as will be seen from the description of the exemplary devices of FIGS. 3 through 5, can serve as a base structure 10 into which the therapeutic composition can be integrated. The device 10 is generally annular and, in the embodiment illustrated, is annular about a central axis 18 and lies in a plane 20 that is perpendicular to that axis. As used herein, the term "annular" as it is used to describe the drug delivery device or structure thereof does not require that the device be a continuous uninterrupted ring but must form substantially an entire ring that can sufficiently extend about the cornea and/or conjunctiva of the eye to maintain the device upon the conjunctiva once provided to an individual. Preferably the annular device forms or substantially forms a ring (i.e., forms at least 60% and more preferably at least 80% of a ring that is designed to extend about the cornea). It should be understood that the area internal to the annular device is typically entirely open allowing for clear vision. However, it is contemplated that a material may be located internal of the annular device. For example, a clear polymeric film material (e.g., a contact lens material or material like a contact lens) might be located internal of the annular device and connected to the device.

In the embodiment shown, the structure 10 is in a continuous ring or band having an inner diameter 22 and an outer diameter 24. Moreover, the illustrated structure 10 is substantially or entirely symmetrical about the central axis 18. The inner diameter is typically configured to be directly adjacent the cornea upon application of the device to the eye. A portion of the device may reside upon the outer periphery of the cornea, but this is typically not desired. The inner diameter of the device is typically at least 0.3 centimeter (cm), more typically at least 0.6 cm and even more possibly at least 0.9 cm and is typically no greater than 1.5, more typically no greater than 1.3 cm and even more typically no greater than 1.1 cm. The outer diameter is typically at least 0.6 cm, more typically at least 1.1 cm and even more possibly at least 1.3 cm and is typically no greater than 2.2, more typically no greater than 1.9 cm and even possibly no greater than 1.7 cm. It should be understood that, for individuals with smaller eyes such as children at ages approximately 3 to 10, these sizes may be reduces by 5 to 20%.

The structure 10 generally has an outer surface 26. That outer surface 26 includes a first surface 28, which is a contacting surface that contacts the conjunctiva of the eye when the structure 10 is placed atop the conjunctiva. The structure 10, and particularly the outer surface 26, also includes a second surface 30 that is opposite the first surface 28. The second surface 30 is an outwardly facing surface that faces away from the conjunctiva upon placement of the device 10 thereon. The first surface 28 can be flat or slightly concave. The second surface 30 can be flat or slight convex. Both the first surface 28 and the second surface 30 are disposed at an angle 34 relative to the plane 20 in which the device 10 lies. That angle 34 may be different for different portions of the surface[s] 26, 28, but is typically at least about 3°, more typically at least about 10° and even possibly at least about 20° and is also typically no greater than about 60°, more typically no greater than about 45° and even possibly no greater than about 30°.

The structure of the device is preferably formed of a non-biodegradable polymer that is substantially or entirely impermeable to the therapeutic composition. Examples of potential materials suitable for the structure include, without limitation, ethylene vinyl acetate (EVA), polyacrylic materials (e.g., PMMA), silicone, polyimide, polytetrafluoroethylene (PTFE), combination thereof or the like. In a highly preferred embodiment, the structure is formed of parylene. As used herein, "substantially impermeable" as it applies to the structure material and the therapeutic composition means that less than 5% and more typically less than 2% of the therapeutic composition permeates into the structure material during the use of the device once applied to an eye of an individual.

With reference to FIG. 3, there is illustrated one exemplary embodiment of a pulsatile peri-corneal drug delivery device 40 in accordance with the present invention. As can be seen, the device 40 has the structure 10 substantially described relative to FIGS. 1 and 2. The device 40 includes multiple reservoirs 42 that each contains a separate and distinct unit 44 of therapeutic composition. Each of the reservoirs 42 is also associated with an opening 46 that can provide for fluid communication between the reservoir 42 and the environment external of the reservoir 42 and the device 40. A plurality of doors 48 is then associated respectively with each of the plurality of openings 46 for controlling flow of fluid through the openings 46. The device 40 also includes an electrical supply 48 (e.g., a battery or battery and controller) and electrical connections 50 that connect to the electrical supply 48 and are connected to or associated with the doors 48.

Typically, the device 40 will include at least 3, more typically at least 10, even more typically at least 60 and even more typically at least 180 and even possibly at least 360 or even at least 600 units 44.

In operation (i.e., after application of the device to an eye of a mammal, particularly a human being), the electrical supply sends electrical current through the connections 50. That electrical current then opens the doors 48 to allow fluid communication between the reservoirs 42 and the environment outside the device 40 to allow the distinct units 44 to be separately released as doses of therapeutic composition at separate points in time. Preferably, each door 48 is configured to allow such fluid communication starting at a separate and distinct point in time. For example, after a first door 48 of the multiple doors 48 opens to provide such fluid communication, each subsequently opening door 48 of the remaining multiple doors 48 will provide such fluid communication at least 60 minutes, more typically at least 8 hours, still more typically at least 10 hours and even possibly at least 20 or even 30 hours after a previously opening door 48 of the multiple doors 48 provides such fluid communication. Such a progression of opening doors 48 will typically continue over an extended period of time.

It is contemplated that the electrical current may open the doors by a variety of mechanisms. Typically, the electrical connections will include an anode and cathode that can induce a charge on opposite side of the door and/or can run the electrical current through the door. In that instance, the doors may be formed of material that erodes or melts upon exposure to the electrical current. Alternatively, the doors could be formed of a material that is drawn toward the anode or cathode upon exposure to electrical charge. The doors could also be formed of a material (e.g., a metal or polymeric material) that vaporizes upon exposure to electrical current or charge.

With reference to FIG. 4, there is illustrated another exemplary embodiment of a pulsatile peri-corneal drug delivery device 60 in accordance with the present invention. As can be seen, the device 60 has the structure 10 substantially described relative to FIGS. 1 and 2. The device 60 includes multiple reservoirs 62 that each contains a separate and distinct unit 64 of therapeutic composition. Each of the reservoirs 62 is also associated with an opening 66 that can provide for fluid communication between the reservoir 62 and the environment external of the reservoir 62 and the device 60. Each of the openings 66 is initially blocked from such fluid communication by a door 68.

In FIG. 4, each of the doors 68 is formed of a bio-erodible material. Examples of such bio-erodible materials include, without limitation, polylactic acids, polyglycolic acids, polylactic-glycolic acids, poly caprolactones, triglycerides, polyethylene glycols, poly orthoesters, poly anhydrides, polyesters, cellulosics and combinations thereof. Moreover, such materials may be applied and may be applied in one or multiple layers by a variety of techniques such as coatings, brushing or the like. In one preferred embodiment, the material of the doors is applied in multiple layers by repeat spray coating and/or drying. It is noted that the doors 68 shown in FIG. 4 are shown in a magnified manner to show them as having different layers. However, it should be understood that the layers will not typically extend outwardly any significant distance from the annular body of the device and are preferably located within the openings 66 to the reservoirs 62.

In operation (i.e., after application of the device to an eye of a mammal, particularly a human being), the doors 68 erode away to allow fluid communication between the reservoirs 62 and the environment outside the device 60 to allow the distinct units 64 to be separately released as doses of therapeutic composition at separate points in time. Preferably, each door 68 is configured to allow such fluid communication starting at a separate and distinct point in time. For example, after a first door 68 of the multiple doors 68 opens to provide such fluid communication, each subsequently opening door 68 of the remaining multiple doors 68 will provide such fluid communication at least 60 minutes, more typically at least 8 hours, still more typically at least 10 hours and even possibly at least 20 or even 30 hours after a previously opening door 68 of the multiple doors 68 provides such fluid communication. Such a progression of opening doors 68 will typically continue over an extended period of time.

In the embodiment shown, each of the doors 68 is shown to have a different thickness. In this manner, the bioerodible material of the doors 68 is configured to allow for fluid communication as described in the preceding paragraph. Preferably, the first door 68 to allow fluid communication will have a thickness ($T_1$). Then each subsequently opening door will have a thickness according to the following equation:

$$T = T_1(N+1)F$$

wherein:

(N) is number of doors 68 that are, or are configured to open and provide or allow fluid communication prior to that subsequently opening door 68; and (F) is any number greater than 0.1 but less than 10 and may be different for each subsequently opening door.

It should be understood that (F) is a variable of the equation that allows for variations in bio-erosion rates and/or preselected pattern of release of the units of therapeutic composition. Typically, the device will include at least 3, more typically at least 10, even more typically at least 60 and even more typically at least 180 and even possibly at least 360 or even at least 600 units 44 and/or reservoirs 42.

With reference to FIG. 5, there is illustrated yet another exemplary embodiment of a pulsatile peri-corneal drug delivery device 80 in accordance with the present invention. As can be seen, the device 80 has the structure 10 substantially described relative to FIGS. 1 and 2. The device 80 includes multiple distinct units 82 of therapeutic composition located within a single annular reservoir 84 that extends substantially entirely about the structure 10. As can be seen, the units are unconnected relative to each other. As can be seen, the distinct units 82 are distributed along the reservoir 84 one after the other. In the particular embodiment shown, spacer units 86 separate the distinct units 82 from each other. When used, the spacer units 86 can aid discrete and separate dispensing and delivery of the distinct units 82 of therapeutic composition.

The device 80 of FIG. 5 also includes an opening 90 and an electromechanical mechanism 92 for providing for fluid communication between at least a portion of the reservoir 84 and the environment external of the reservoir 84 and the device 80. As can be seen, the electromechanical mechanism 92 can move the discrete units 82 and/or the spacer units 86 about the reservoir 84 to individually align each discrete unit 82 with the opening 90. Once a discrete unit 82 has been aligned with the opening 90, fluid communication between the reservoir 84 and the external environment of the device 80 through the opening 90 allows the discrete unit 82 to release its therapeutic composition to that external environment (e.g., tear fluid can enter the reservoir 84 through the opening 90 to allow for such release). Preferably, the electromechanical mechanism 92 is pre-programmed to move the units 82 a separate distinct points in time.

The discrete units 82 can be formed in a variety of configurations that will allow them to relatively rapidly release therapeutic composition when the unit 82 is aligned with the opening 90. In a preferred embodiment, the discrete units are comprised of a non-biodegradable material (e.g., polymeric material) that includes one or more openings and or reservoirs for containing and then releasing the therapeutic composition. As one example, the discrete unit 82 can comprise a shell (e.g., a polymeric shell) substantially surrounding a reservoir, which contains the therapeutic composition in a solid, but dissolvable, form. In such an embodiment the shell will typically include one or more openings such that fluid (e.g., tear fluid) can enter the opening[s] and/or reservoir and dissolve the therapeutic composition, which can then be released from the polymeric shell. As another example, the discrete unit 82 comprises a non-erodible body that has a coating of therapeutic composition on it and fluid (e.g., tear fluid) can dissolve the therapeutic composition, which can then be released from the body. In such an embodiment, the coating of therapeutic composition could include a polymeric material that is either erodible or non-erodible, but which can aid in controlling the rate of release of the therapeutic composition from the distinct unit. As still another example, the discrete unit 82 comprises a non-erodible matrix (e.g., polymeric matrix) within which a therapeutic composition has been dispersed. In such an embodiment, the therapeutic composition can permeate out of the matrix when it is exposed to fluid (e.g., tear fluid) adjacent the opening of the device. Typically, the device 80 will include at least 3, more typically at least 10, even more typically at least 60 and even more typically at least 180 and even possibly at least 360 or even at least 600 units 84.

A variety of mechanisms may be suitable for use as the electromechanical mechanism 92 for the device 80. For example, a small electrical powered gear system might be used to advance the units 82. Alternatively, a small magnetic system could be used to advance the units 82. Preferably, the mechanism includes a controller for controlling the system such that it advances the units 82 at predetermined times.

In operation (i.e., after application of the device to an eye of a mammal, particularly a human being), the discrete units 82 are individually moved to the opening 90 to progressively allow fluid communication between each of the units 82 and the environment outside the device 80 to allow the distinct units 82 to separately release doses of therapeutic composition at separate points in time. Preferably, each of the units 82 are moved about the reservoir 84 to align one of the units with the opening 82 at distinct points in time that are at least 60 minutes, more typically at least 8 hours, still more typically at least 10 hours and even possibly at least 20 or even 30 hours apart from each other to allow each of the units to release therapeutic composition to the environment outside the device 80. Such a progression of release from the units 82 will typically continue over an extended period of time.

In an alternative configuration, it is contemplated that the device of the present invention can configured substantially identical to the device 80 of FIG. 5 with minor exceptions. The therapeutic composition can be provided as a single, preferably liquid, mass or supply that can be released through the opening 90 as separate and distinct units. In such an embodiment, the flow through the opening would be controlled by a door or valve that would allow for release of portions of the single mass or supply of therapeutic compositions at separate points in time to form the separate and distinct doses or units.

The therapeutic composition of the present invention will typically include a therapeutic agent and may be consist or consist essentially of only therapeutic agent. Alternatively, the therapeutic composition can include one or more excipients such as, surfactant, tonicity agent, carrier such as water, polymeric material (e.g., biodegradable polymeric material), antimicrobial agent, buffering agents, combinations thereof or the like. The therapeutic composition may be provided as a liquid, semi-solid or solid, which will typically depend upon the type of discrete units, door[s] and/or reservoir[s] used with the device. Preferably, the therapeutic composition, particularly the therapeutic agent, is in a condition that allows it to, upon release from the device to the environment external the eye (e.g., to the tear fluid). The therapeutic composition, particularly the therapeutic agent, can then move with the tear fluid to the conjunctiva and/or to the cornea and/or to the back of the eye. The therapeutic composition, particularly the therapeutic agent, can then penetrate into the eye or treat a surface disease of the eye.

The therapeutic agent (e.g., ophthalmic drug) may be any therapeutic agent, so long as the therapeutic agent is capable of providing a therapeutic effect to the eye of a mammal, particularly a human. In particular embodiments, the therapeutic compound is a compound that can be applied for the treatment of an ophthalmic disorder. For example, the therapeutic compound may be a glaucoma medication, an antimicrobial medication, an anti-inflammatory medication, or a dry-eye syndrome medication, or a therapeutic compound that can be applied in the treatment of diabetic retinopathy or age-related macular degeneration.

Ophthalmic drugs, such as prostaglandins, triamcinolone, 15-HETE (Icomucret), anti-inflammatories (non-steroidal anti-inflammatory drugs (NSAIDs)) receptor tyrosine kinase inhibitors (RTKi), timolol maleate, fluoroquinolones (e.g., moxifloxacin) and rimexolone, are well suited for delivery with the devices of the present invention. The prostaglandin may be a natural or a synthetic prostaglandin. Non-limiting examples of prostaglandins include cloprostenol, fluprostenol, latanoprost, travoprost, and unoprostone.

It is also contemplated that the device of the present invention may be use to deliver multiple therapeutic agents. For example, for one device, a first one or subset of the distinct doses or units may include a therapeutic composition having a different therapeutic agent than another second one or subset or subset of distinct doses or units. Moreover, those units can be delivered at any distinct points in time to provide a desired therapy.

According to certain aspects of the present invention, the opening[s] that allow for fluid communication to the reservoir[s] and/or therapeutic composition are located only on the surface of the device that contacts the conjunctiva of the eye. Alternatively, the opening[s] can be located only on the surface facing away from the conjunctiva of the eye. As still another alternative, opening[s] may be located on both surfaces. Having opening[s] facing away from the conjunctiva can be particularly desirable for delivery of anti-glaucoma or intraocular pressure lowering therapeutic agents such as a prostaglandin (e.g., cloprostenol, fluprostenol, latanoprost, travoprost, and unoprostone). This allows the therapeutic agent to diffuse into the tear fluid and from the tear fluid through the cornea to the iris ciliary body. Having opening[s] that face and/or contact the conjunctiva can be particularly desirable for therapeutic agents that act at the posterior of the eye and can benefit from improved delivery to the vitreous. Such drugs can include anti-inflammatories, particularly NSAIDs such as nepafenac or diclofenac.

In certain aspects, the devices of the present invention deliver multiple separate therapeutically effective doses of the therapeutic composition to a mammal, particularly a human being, over an extended time period. As used herein, the phrase "extended time period" is no less than 12 hours, but is typically at least about 24 hours, at least about 5 days, at least about 20 days, at least about 30 days, at least about 60 days, at least about 90 days, at least about 120 days, at least about 180 days, at least about 240 days or any range derivable therein. In particular embodiments, the devices of the present invention deliver the therapeutically effective doses of the therapeutic composition for at least 10 days.

Advantageously, the device of the present invention can provide desirable dosage amounts of therapeutic agent during the above referenced extended time periods. Generally, the device can typically deliver doses that includes at least 0.01 μg, more typically at least 0.1 μg and even more typically at least 0.6 μg of therapeutic agent per dose or distinct unit. The device also typically delivers no greater than 1000 μg, more typically no greater than 400 μg and still more typically no greater than 150 μg of therapeutic agent per dose or distinct unit. For higher potency drugs such as prostaglandins, the device is typically configured to deliver from about 0.4 μg to about 2.0 μg of therapeutic agent per dose or distinct unit. For medium potency drugs, the device is typically configured to deliver from about 5 to about 20 μg. For lower potency drugs, the device is typically configured to deliver from about 30 μg to about 120 μg of therapeutic agent per dose or distinct unit.

In one embodiment, the present invention provides a method of treating an ocular disorder in a subject comprising: (a) forming a drug delivery device as described herein for the sustained release of multiple separate doses of therapeutic composition to the eye; and (b) disposing the device upon an external surface (e.g., surface of the conjunctiva) of the eye. The method can be specifically for treating glaucoma or ocular hypertension in a subject (e.g., a human) and the therapeutic agent can be, for example, a prostaglandin.

In some embodiments, biodegradable microspheres of the therapeutic agent are formed for creating the whole or a part of the therapeutic composition. Microspheres, microcapsules and nanospheres (collectively, "microspheres") are generally accepted as particles with diameters ranging from approximately 50 nm to 1000 micrometers. They are reservoir devices that come in a variety of different forms, including, but not limited to, porous, hollow, coated, or uncoated forms with a pharmaceutically active agent either incorporated into or encapsulated by polymeric material via numerous known methods. Such known methods include, but are not limited to, spray drying, spinning disk and emulsification methods. Microspheres may be formed from a myriad of polymeric materials selected from, but not limited to, polylactic acids, polyglycolic acids, polylactic-glycolic acids, poly caprolactones, triglycerides, polyethylene glycols, poly orthoesters, poly anhydrides, polyesters, cellulosics and combinations thereof. The amount of therapeutic agent incorporated or encapsulated in the microsphere is generally between 0.001% and about 50%.

The device can be configured to have a relatively large external surface area, which allows the device to be maintained upon the conjunctiva more securely. In particular, capillary forces of the fluid upon the conjunctiva can aid in maintaining the device upon the eye. It should be noted that, for purposes of this invention, the fluid located upon the conjunctiva is considered to be part of the conjunctiva upon which the device can be located. The surface area of the contacting surface as determined inclusive of any and every portion (including haptics) of the device that contacts the conjunctiva is typically at least 50 (millimeters squared) $mm^2$, more typically at least 77 $mm^2$, even more typically at least 90 $mm^2$ and even possibly at least 110 $mm^2$ and the surface area of that portion is typically no greater than 320 $mm^2$, more typically no greater than 220 $mm^2$, even more possibly no greater than 170 $mm^2$ and even possibly no greater than 120 $mm^2$.

Advantageously, it may be the case that the device of the present invention can reside upon and be maintained upon the eye without needing any fastening elements such as stitches or other mechanical devices that extend into the eye (i.e. into the conjunctiva, cornea or any other portion of the eyeball). Such fastening devices typically must be surgically applied and avoidance of such surgical applications can be desirable in many circumstances.

The device of the present invention can, in certain embodiments, be relatively large such that it can include multiple doses or distinct units of therapeutic composition. The volume of the entire device of the present invention is typically at least 10 $mm^3$, more typically at least 14 $mm^3$, and even more typically at least 18 $mm^3$ and the volume of the device is typically no greater than 100 $mm^3$, more typically no greater than 50 $mm^3$, and even possibly no greater than 30 $mm^3$. The weight of the entire device of the present invention is typically at least 10 mg, more typically at least 14 mg, and even more typically at least 17 mg and the weight of the device is typically no greater than 1000 mg, more typically no greater than 100 mg, and even more possibly no greater than 30 mg.

The use of the term "or" in the claims is used to mean "and/or" unless explicitly indicated to refer to alternatives only or the alternatives are mutually exclusive.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

In this document (including the claims), the terms "comprise" (and any form of comprise, such as "comprises" and "comprising"), "have" (and any form of have, such as "has" and "having"), and "include" (and any form of include, such as "includes" and "including") are open-ended linking verbs.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the to invention being indicated by the following claims and equivalents thereof.

We claim:

1. An ophthalmic pericorneal drug delivery device, comprising:
    an annular body sized and shaped to reside upon a conjunctiva of a human eye and extend substantially entirely about a cornea of the human eye when the annular body is disposed upon the human eye;
    a therapeutic composition associated with the annular body wherein the therapeutic composition is disposed as multiple separate distinct units in a single reservoir within the annular body;
    an electromechanical device connected to the annular body; and
    at least one opening for providing fluid communication between the single reservoir and an environment external of the device wherein the electromechanical device moves each unit to the at least one opening at a separate point in time over an extended time period.

2. A device as in claim 1 wherein each of the separate and distinct units comprises a polymeric shell defining at least one reservoir wherein the therapeutic composition is disposed in the at least one reservoir of the polymeric shell of each of the separate and distinct units.

3. A device as in claim 1 wherein the separate and distinct units comprise a body with a therapeutic composition coated thereon.

4. A device as in claim 1 wherein the separate and distinct units comprise a polymeric matrix with therapeutic composition dispersed throughout the matrix.

5. A device as in any of claims 1 through 4 wherein the reservoir is annular and the separate and distinct units are distributed about the reservoir.

6. A device as in claim 1 wherein the therapeutic composition includes a prostaglandin.

7. A device as in claim 1 wherein the device, the annular body or both include a contact surface that is shaped and sized to correspond to and contact the conjunctiva of the human eye upon application of the device to the eye.

8. A device as in claim 7 wherein the contact surface of the device including all portions that contact the conjunctiva has a surface area that is at least 77 $mm^2$ and is typically no greater than 220 $mm^2$.

9. A device as in claim 8 wherein the device has a volume that is at least 14 $mm^3$ and is no greater than 100 $mm^3$.

10. A method of treating an ophthalmic disease comprising:
    disposing a device as in claim 1 on the conjunctiva of the eye.

11. A method as in claim 10 wherein the device is maintained upon the eye for an extended period of time that is at least 24 hours.

* * * * *